(12) United States Patent
Zhang et al.

(10) Patent No.: US 7,858,192 B2
(45) Date of Patent: *Dec. 28, 2010

(54) GRADED GLASS/CERAMIC/GLASS STRUCTURES FOR DAMAGE RESISTANT CERAMIC DENTAL AND ORTHOPEDIC PROSTHESES

(75) Inventors: Yu Zhang, Chatham, NJ (US); Jae-Won Kim, Elmhurst, NY (US); Van P. Thompson, New York, NY (US)

(73) Assignee: New York University, New York, NY (US)

( * ) Notice: Subject to any disclaimer, the term of this patent is extended or adjusted under 35 U.S.C. 154(b) by 248 days.

This patent is subject to a terminal disclaimer.

(21) Appl. No.: 11/986,290

(22) Filed: Nov. 20, 2007

(65) Prior Publication Data
US 2008/0213727 A1    Sep. 4, 2008

(51) Int. Cl.
*B32B 17/06* (2006.01)
(52) U.S. Cl. .................. 428/432; 428/426; 428/428
(58) Field of Classification Search ............ 428/426, 428/428, 432
See application file for complete search history.

(56) References Cited

U.S. PATENT DOCUMENTS

| | | |
|---|---|---|
| 6,641,893 B1 | 11/2003 | Suresh et al. |
| 2003/0029910 A1* | 2/2003 | Goretta et al. ............ 228/248.1 |
| 2005/0027195 A1 | 12/2005 | Moini et al. |
| 2006/0191916 A1 | 8/2006 | Stephan et al. |

* cited by examiner

*Primary Examiner*—Gwendolyn Blackwell
(74) *Attorney, Agent, or Firm*—Klauber & Jackson, LLC

(57) ABSTRACT

The present invention provides a functionally graded glass/ceramic/glass sandwich system especially useful in damage resistant, ceramic dental and orthopedic prosthesis. The functionally graded glass/substrate/glass composite structure comprises an outer (aesthetic) residual glass layer, a graded glass-ceramic layer, and a dense interior ceramic. The functionally graded glass/substrate/glass composite structure may further comprise a veneer on an exterior surface. The present invention also provides a method for preparing a functionally graded glass/ceramic/glass sandwich system. A powdered glass-ceramic composition or a glass tape is applied to the accessible surfaces of a dense alumina substrate to thereby substantially cover the substrate surfaces. The glass of the composition has a CTE similar to that of the substrate material. The glass-ceramic composition is infiltrated into the dense substrate by heating the assembly to temperatures 50-700° C. below the sintering temperature of the substrate.

10 Claims, 6 Drawing Sheets

FIG. 4B — Alumina grain, Grain boundary glass phase, 5 μm

FIG. 4C — Alumina grain, Grain boundary glass phase, 5 μm

GRADED GLASS/CERAMIC/GLASS STRUCTURES FOR DAMAGE RESISTANT CERAMIC DENTAL AND ORTHOPEDIC PROSTHESES

FIELD OF THE INVENTION

The present invention relates to dental and orthopedic prostheses and methods for producing improvements in dental and orthopedic prostheses using functionally graded materials ("FGMs") such as a functionally graded glass/ceramic/glass (G/C/G) material, especially a glass/alumina/glass (G/A/G) sandwich material.

BACKGROUND OF THE INVENTION

Teeth play a critically important role in our lives. Loss of function reduces the ability to eat a balanced diet which results in negative consequences for systemic health. Loss of aesthetics can negatively impact social function. Both function and aesthetics can be restored with dental crowns and bridges. Ceramics are attractive dental restoration materials because of their aesthetics, inertness, and biocompatibility. However, ceramics are brittle and subject to premature failure, especially after repeated contact including slide-liftoff masticatory loading in a moist environment (Kim et al. (2007) *Journal of Dental Research* 86(11): 1046-1050; Lawn et al. (2001) *The Journal of Prosthetic Dentistry* 86(5): 495-510; Lawn et al. (2001) *J Prosthet Dent* 86(5): 495-510; Zhang et al. (in press) "Fatigue Damage in Ceramic Coatings from Cyclic Contact Loading with Tangential Component." *Journal of the American Ceramic Society*) Fracture rates of ceramic restorations may seem low at 3-4% per year (Fradeani et al. (1997) *Int. J. Prothodont.* 10: 241-7; Malament et al. (1999) *J. Prosthet. Dent.* 81: 23-32; Sjogren et al. (1999) *Int. J. Prosthodont.* 12: 122-8; Sailer et al. (2006) *Quintessence International* 37(9): 685-693; Sailer et al. (2007) *Clin. Oral Impl. Res.* 18(3): 86-96; Pjetursson et al. (2007) *Clin. Oral Impl. Res.* 18(3): 73-85). However, failure can cause significant patient discomfort and loss of productive lifestyle. The vulnerability of dental ceramic restorations is exacerbated by damage, fatigue loading, and moisture.

According to a survey conducted by American Dental Association, more than 45 million new dental crowns, of which over 37 million were porcelain (ceramic) based, were provided by dentists in 1999 (ADA (2002). "The 1999 Survey of Dental Services Rendered."). As the population ages, the number will increase. Despite continuous efforts to improve the strength of dental ceramics, all-ceramic dental crowns continue to fail at a rate of approximately 3-4% each year (Burke et al. (2002) *J Adhes Dent* 4(1): 7-22). The highest fracture rates are on posterior crowns and bridges where stresses are greatest. Dental crowns generate over $2 billion each year in revenues with 20% of the units being all-ceramic (Nobel Biocare 2004). Dental ceramics that best mimic the optical properties of enamel and dentin are predominantly glassy materials principally feldspar (a group of minerals having main constituents of silica and alumina) (Kelly (1997) *Annual Reviews of Materials Science* 27: 443-68; Kelly (2004) *Dent. Clin. N. Am.* 48: 513-30). The original dental porcelain contained high feldspathic glass content and was extremely brittle and weak (S (strength) approximately ~60 PMa) (McLean, J. W. (1979) *The Science and Art of Dental Ceramics*. Chicago, Quintessence Publishing Co. Inc.; Binns, D. (1983) *The Chemical and Physical Properties of Dental Porcelain*. Chicago, Quintessence Publishing Co. Inc.). Therefore, despite the aesthetic advantage, the early porcelain crowns were not widely used in dentistry (Van, N. R. (2002). "An Introduction to Dental Materials." 231-46).

Today, about 0.1% of the population in North America and Europe need a total hip replacement (THR), and over 300,000 total knee replacement surgeries are performed each year in the United States. (Willmann G. Ceramics for Total Hip Replacement—What a Surgeon Should Know. 1998, 21(2): 173-7:NIH, *J Bone Joint Surg Am* 2004;86-A(6):1328-1335) The overall orthopedic implants, including replacement of knees, hips, fingers, and spinal processes, are estimated to have a world-wide market exceeding $4.3 billion annually. (Davis J R. Handbook of materials for medical devices materials. Park, Ohio; 2003). On the other hand, dental crowns and bridges generate over $2 billion each year in revenues with 20% of the units being all-ceramic. (Dental Market Overview Nobel Biocare; 2004) The demand for aesthetics will likely drive the number of all-ceramic prostheses even higher. Despite a continuous effort in improving the properties of medical and dental ceramics, ceramic prostheses are still vulnerable to wear and surface damage, especially in repeated loading in wet environments. Wear characteristic and catastrophic failure of ceramic-on-ceramic articulations continue to be a concern. (Barrack et al., *Clinical Orthopaedics and Related Research* 2004;429:73-79) All-ceramic dental crowns, including porcelain-veneered alumina and zirconia, continue to fail at a rate of approximately 1-3% each year. (Burke et al., *J Adhes Dent* 2002;4(1):7-22; Sailer et al., *Clin. Oral Impl. Res.* 2007;18(3):86-96)

Dental ceramics have become increasingly popular as restorative materials due to improvements in strength. Several methods have been developed to improve the strength of dental ceramics including adding uniformly disperse appropriate filler particles throughout a glass matrix, referred to as "dispersion strengthening" (McLean et al. (1965) *Br. Dent. J.* 119: 251-67). The first fillers used in dental ceramics were leucite particles (Denry (1996) *Crit. Rev. Oral. Biol. Med.* 7: 134-43). Commercial dental ceramics containing leucite as a dispersion strengthening fillers include IPS Empress (S approximately 120 PMa) (Ivoclar-Vivadent, Schaan, Liechtenstein) and Finesse All-ceramic (S approximately 125 MPa) (Dentsply Prosthetics, York, Pa.). Particle strengthening can also be achieved by heat-treating the glass to facilitate the precipitation and subsequent growth of crystallites within the glass, termed "ceraming". Dental ceramics produced using the ceraming process are called glass-ceramics. Several commercial products such as Dicor (S approximately 160 MPa) (Dentsply), IPS Empress II (S approximately 350 MPa) (Ivoclar-Vivadent) and, more recently, IPS e.max Press (S approximately 525 MPa) (Ivoclar-Vivadent) are examples. The leucite-strengthened porcelains and the glass-ceramics are translucent, so single layer (monolithic) crowns can be made from these materials. However, only moderate strength increases can be achieved via the particle strengthening techniques. Therefore, monolithic ceramic crowns experience high failure rates range from 4-6% for Dicor molar crowns (Malament et al. (1999) *J. Prosthet. Dent.* 81: 23-32) and 3-4% per year for IPS Empress crowns (Fradeani et al. (1997) *Int. J. Prothodont.* 10: 241-7; Sjogren et al. (1999). *Int. J. Prosthodont.* 12: 122-8). Note: comprehensive clinical reports on the new IPS e.max Press crowns are not available at this stage.

The current approach to the fracture problem of monolithic crowns is a layer-structure with aesthetic but weak porcelain veneers fused onto strong but opaque ceramic cores. This involves an increase in crystalline content (from approximately 40 vol. % to 99.9 vol. %) accompanied by a reduction in glass content. The first successful strengthened core ceramic was made of feldspathic glass filled with approximately 40 vol % alumina particles (McLean et al. (1965). *Br. Dent. J.* 119: 251-67). The alumina fillers increased the flexural strength of the ceramic to approximately 120 MPa with a trade off in translucency; hence veneering was required. Using McLean's approach, in 1983 Coors Biomedical (Golden, Colo.) developed Cerestore all-ceramic crowns with a ceramic core containing approximately 60 vol. % of alumina (Sozio et al. (1983). *J. Prosthet. Dent.* 69: 1982-5). However, following problems with fractured crowns the manufacturer withdrew the system. A similar product from the same era, the Hi-Ceram crown (Vita, Bad Säckingen, Germany) with its core material containing about the same amount of alumina as the Cerestore core, also failed to meet the satisfactory for posterior restorations (Bieniek et al. (1994). *Schweitz Monatsschr Zahnmed* 104: 284-9). The Hi-Ceram crown was replaced by In-ceram crown (Vita) in 1990. The In-ceram crown had a core that was fabricated by lightly sintering an alumina powder compact and then infiltrating the still porous alumina matrix with a low viscosity glass. The final core material contained approximately 70 vol. % of alumina and had a flexural strength of approximately 450 MPa (Probster (1992) *Int J Prosthodont* 5(5): 409-14). In 1993, Procera (Nobel Biocare, Göteborg, Sweden) presented the all-ceramic crown concept (Anderson et al. (1993). *Acta Odontol Scand* 51: 59-64), where the fully dense core material contained 99.9 vol % alumina and displayed a flexural strength of 675 MPa. Several years later, even stronger Y-TZP ceramic was introduced to dentistry as a core material with a flexural strength over 1200 MPa.

Unfortunately, no current materials, including stronger monolithic ceramics (orthopedic and dental prostheses) or strong cores to support weak, but aesthetic porcelain veneers (dental prostheses) can effectively suppress both contact and flexural damages. In addition, veneered strong ceramic dental prostheses have a dense, high purity crystalline structure at the cementation internal surface that cannot be readily adhesively bonded to tooth dentin as support. Surface roughening treatment such as particle abrasion is commonly used to enhance the ceramic-luting agent bond. However, particle abrasion also introduces surface flaws or microcracks that can cause deterioration in the long-term flexural strength of ceramic prostheses. (Zhang et al. (2004) *Journal of Biomedical materials research* 71B(2): 381-6; Zhang et al. (2005) *Journal of Biomedical materials research* 72B: 388-92; Zhang et al. (2006) *The International Journal of Prosthodontics* 19(5): 442-8).

Recent advances in theoretical and experimental work have shown that functionally graded materials, referred to as FGMs, may provide unprecedented resistance to contact damage (Suresh et al. (2003) U.S. Pat. No. 6,641,893; Suresh et al. (1997) *Acta Materialia* 45(4): 1307-21; Jitcharoen et al. (1998) *Journal of the American Ceramic Society* 81(9): 2301-8; Suresh et al. (1999) *Acta Materialia* 47(14): 3915-3926). Such damage resistance cannot be realized with conventional homogeneous materials. FGMs are made of two materials that are combined so that the surface of the FGM is composed entirely of material A, and the interior is composed entirely of material B. Additionally, there is a continuous change in the relative proportions of the two materials from the surface to interior. One known FGM is a thick ceramic block, alumina or silicon nitride, infiltrated with a low elastic modulus aluminosilicate glass or oxynitride glass (SiAlYON), respectively, on one surface to produce a graded glass/ceramic (G/C) structure that suppresses contact damage at the top, occlusal surface (Jitcharoen et al. (1998) *Journal of the American Ceramic Society* 81(9): 2301-8). However, upon infiltration of dense ceramics, the glass penetrates the grain boundaries and grain boundary triple junctions, and as a result, the ceramic grains gradually separate. This leads to an increase in volume at the surface of graded structure and is accompanied by warpage or bending of the specimens where the glass-impregnated surface is convex.

Aluminium oxide is an amphoteric oxide of aluminium with the chemical formula $Al_2O_3$. It is also commonly referred to as alumina in the mining, ceramic and materials science communities. It is produced by the Bayer process from bauxite; its most significant use is in the production of aluminium metal. Being very hard, it is used as an abrasive. Having a high melting point, it is used as a refractory material. Aluminium oxide is an electrical insulator but has a relatively high thermal conductivity. In its most commonly occurring crystalline form, called corundum or α-aluminum oxide, its hardness makes it suitable for use as an abrasive and as a component in cutting tools. Aluminium oxide is responsible for metallic aluminium's resistance to weathering. Metallic aluminium is very reactive with atmospheric oxygen, and a thin passivation layer of alumina quickly forms on any exposed aluminium surface. This layer protects the metal from further oxidation. The thickness and properties of this oxide layer can be enhanced using a process called anodising. A number of alloys, such as aluminium bronzes, exploit this property by including a proportion of aluminium in the alloy to enhance corrosion resistance. The alumina generated by anodising is typically amorphous, but discharge assisted oxidation processes such as plasma electrolytic oxidation result in a significant proportion of crystalline alumina in the coating, enhancing its hardness.

SUMMARY OF INVENTION

The present invention takes advantage of the discovery that fracture problems of ceramic prostheses are minimized by a new generation of damage resistant ceramic prostheses utilizing functionally graded materials (FGMs). The present invention represents an improvement over the G/C structure of the prior art to a graded G/C/G structure by infiltrating top and bottom ceramic surfaces with glass. The present invention features a structure of G/C/G comprising an outer (aesthetic) surface residual glass layer, a graded glass-ceramic layer, and a dense interior ceramic.

In a first aspect, the present invention provides a method for preparing a functionally graded glass/ceramic/glass (G/C/G), preferably a functionally graded glass/alumina/glass (G/A/G) sandwich material, comprising: (a) applying a glass-ceramic composition, preferably a powdered slurry or a glass tape, to accessible surfaces of a ceramic substrate, preferably a fully sintered alumina substrate, thereby covering the ceramic substrate, preferably alumina substrate surfaces with a layer of the composition wherein the coefficient of thermal expansion (CTE) of the glass-ceramic and the coefficient of thermal expansion (CTE) of the substrate material are substantially the same; and (b) infiltrating the glass-ceramic composition into the substrate by heating the substrate to a temperature below the ceramic sintering temperature, preferably below the alumina sintering temperature. In some embodiments, the heating is performed to approximately 50-700° C. below the sintering temperature of the substrate. The methods are also applicable to other ceramic materials, including for instance, $Si_3N_4$, sialons, MgO, spinel, and alumina-zirconia composites, such that the methods may be altered accordingly by merely substituting the same for alumina.

In some embodiments, the substrate comprises fully sintered alumina. In other embodiments, the substrate is densified in one or more firing cycles at a temperature of from about 1000° C. to 1750° C., or 1200° C. to 1700° C., preferably from about 1500° C. to 1650° C. Also, in some embodiments, the powdered glass-ceramic composition is dispersed in an aqueous based solution. In other embodiments, the powdered glass-ceramic composition is used to form a glass tape. It is preferred that the powdered glass-ceramic composition comprises one or more oxides selected from the group consisting of $SiO_2$, $Al_2O_3$, $TiO_2$, $Na_2O$, $K_2O$, ZnO, $Rb_2O$, etc. Each of the one or more oxides may be present in a weight percent of about 1%, 2%, 5%, 10%, 15%, 20%, 25%, 30%, 50%, 60%, 70%, or even 80% or 90%. In some embodiments only of the oxides is present, while in other embodiments, two, three, four, five, six, seven or even eight of the oxides may be present.

Also, in particularly preferred embodiments, the CTE of the glass and the CTE of the ceramic, preferably alumina, are substantially the same. That is, when the CTEs are substantially the same, in some embodiments, the CTE of the glass and the CTE of the ceramic, preferably alumina, are within about 50%, 40%, 30%, 25%, 20%, 10%, 5%, 2%, 1% or even 0.5% or 0.25% of each other. In especially preferred embodiment, the CTE of the glass is approximately about 7.0 to 9.0, or 7.0 in/in/° C., from 0 to 500° C., and the CTE of the ceramic, preferably alumina, is approximately about 7.0 to 9.0, or 7.0 in/in/° C., from 0 to 500° C. In some embodiments, the alumina substrate is sintered such as by a microwave technique, and in some embodiments, the glass/alumina/glass (G/A/G) sandwich material is infiltrated by a microwave technique. In some embodiments the infiltrating step may be performed for about 0 minute, 5 minutes, 10 minutes, 15 minutes, 20 minutes, 30 minutes, 45 minutes, or even 60 minutes, 90 minutes, 120 minutes, 240 minutes or more. In especially preferred embodiments, the infiltrating step is performed for about 60+/−5 minutes at a temperature of about 1000° C. to about 1600° C.

In a second aspect, the present invention provides a functionally graded glass/ceramic/glass composite structure comprising an outer residual glass layer which may be an aesthetic layer, an underlying graded glass-ceramic layer, and a dense interior ceramic. In some embodiments, the functionally graded glass/ceramic/glass composite structure is substantially non-susceptible to warping or bending. The functionally graded glass/ceramic/glass (G/C/G) sandwich material may be produced in some instances by the method described above as a first aspect of the invention. The ceramic material may be any one of many materials, for instance, alumina, $Si_3N_4$, sialons, MgO, spinel, and alumina-zirconia composites. In especially preferred embodiments, the ceramic material is alumina, and the structure is a graded glass/alumina/glass (G/A/G) structure.

In some embodiments, the functionally graded glass/ceramic/glass composite structure is composed of an underlying ceramic made substantially of dense alumina. In some embodiments, the CTE of the glass and the CTE of the alumina are substantially the same. That is, when the CTEs are substantially the same, in some embodiments, the CTE of the glass and the CTE of the alumina are within about 50%, 40%, 30%, 25%, 20%, 10%, 5%, 2%, 1% or even 0.5% or 0.25% of each other. In especially preferred embodiment, the CTE of the glass is approximately about 5.0 to 11.0, 6.0 to 10.0, or 7.0 in/in/° C., from 0 to 500° C., and the CTE of the alumina is approximately about 5.0 to 11.0, 6.0 to 10.0, or 7.0 in/in/° C., from 0 to 500° C.

In some embodiments, the outer glass layer may be from 5 to 1,000 microns thick, sometimes 10 to 750 microns thick, or 20 to 500 microns thick, or 25 to 250 microns thick, or 30 to 100 microns thick, for instance. Likewise, in some embodiments, the graded glass-ceramic layer may be from 10 to 5000 microns thick, or 20 to 2000 microns thick, or 30 to 1000 microns thick, or 40 to 800 microns thick, or 50 to 600 microns thick, for instance. In some instances the graded glass-ceramic layer may be at least about 5%, at least about 10%, at least about 20%, at least about 30%, at least about 40%, at least about 50%, or even 60%, 70%, 80%, 90% or 95% glass. In some embodiments, there is a residual glass layer on the outer surface above the graded glass-ceramic layer, and in other embodiments there is no residual glass layer beyond the graded glass-ceramic layer.

In some embodiments, the functionally graded glass/ceramic/glass composite structure is significantly more resistant to flexure-induced fracture than a homogeneous ceramic structure. That is, in some embodiments, the functionally graded glass/ceramic/glass composite structure may tolerate at least 5%, 10%, 20%, 30%, 50% or even 75% or more critical load than a homogeneous ceramic of the same ceramic material before experiencing fracture.

In a third aspect, the present invention provides a prosthesis comprising a functionally graded glass-ceramic/ceramic/glass-ceramic composite structure or a graded glass-ceramic/ceramic structure. The prosthesis may be, for instance, an aesthetic and damage-resistant ceramic orthopedic prosthesis, orthopedic stems, orthopedic/dental anchors, orthopedic/dental implants, dental prostheses, and endodontic posts. The structure may comprise an outer residual low modulus glass layer which may be an aesthetic layer, an underlying graded glass-ceramic layer, and a dense interior ceramic. The prosthesis preferably comprises a functionally graded glass/ceramic/glass composite structure comprising an outer residual glass layer, an underlying graded glass-ceramic layer, and a dense interior ceramic as described in the second aspect of the invention.

DETAILED DESCRIPTION OF THE INVENTION

Figure 1:
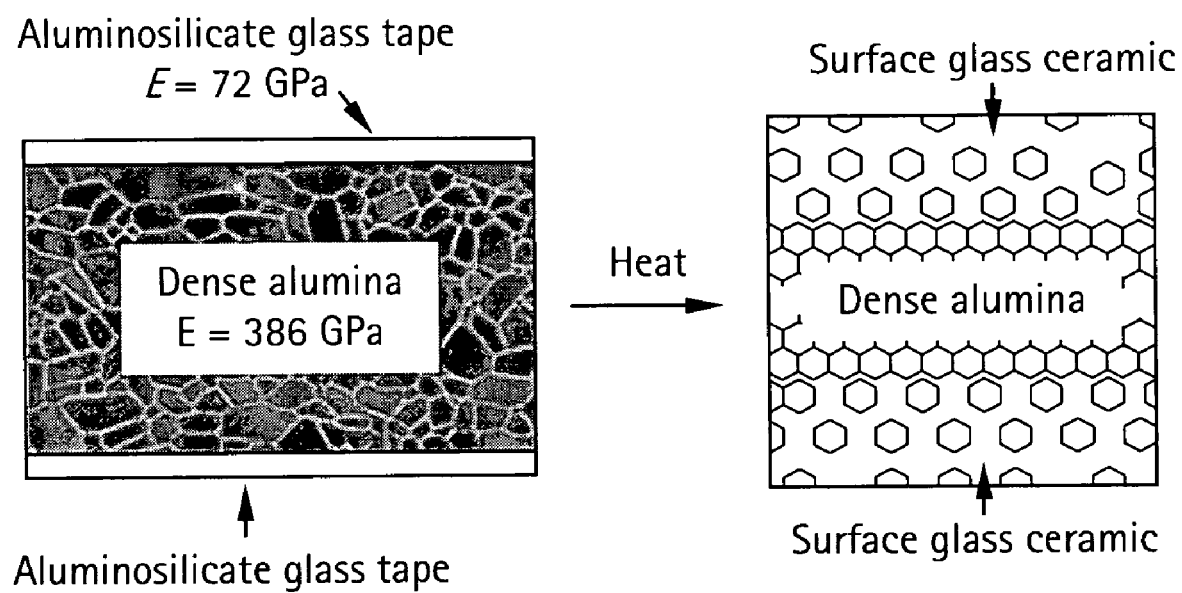
FIG. 1 is a schematic diagram illustrating the processing method for the fabrication of glass/alumina/glass composite with graded structure at both top and bottom surfaces. (1) Applying glass tapes on both top and bottom surfaces of dense alumina plates, and (2) Infiltrating between 1000 to 1700° C. to form a glass/alumina/glass composite.

An FGM structure where a thick ceramic block, alumina or silicon nitride, is infiltrated with a low elastic modulus aluminosilicate glass or oxynitride glass, respectively, on one surface to produce a graded glass/ceramic (G/C) structure that suppresses contact damage at the top, occlusal surface is known in the art. (Jitcharoen et al. (1998) *Journal of the American Ceramic Society* 81(9): 2301-8) The present invention provides a graded G/C/G structure by infiltrating top and bottom ceramic surfaces with glass. The G/C/G structure suppresses both occlusal surface contact damage and cementation internal surface flexural damage.

By "sintering" or "densifying" is meant substantially removing the pores between starting particles thereby shrinking the component combined with growing together and forming stronger bonds between adjacent particles.

By "sintering temperature" is meant a temperature for performing the sintering or densifying process described above. "Sintering" is usually performed at elevated temperatures, typically below the melting point of the substance to be sintered or densified.

By "infiltrating" is meant penetrating a liquid glass or glass-ceramic phase into the grain boundaries and grain boundary triple junctions of a polycrystalline ceramic or composite.

The FGM structure of the present invention having a low modulus glass ceramic at both the top and the bottom surfaces, sandwiching a high modulus, strong ceramic interior, improves resistance to both contact and flexural damage. In addition, the FGM structure of the present invention together with outer surface residual glass layers may be used to enhance the aesthetic properties, as well as the veneering and cementation behaviors of polycrystalline dental ceramic cores, including the exceptionally strong class of zirconia ceramics. Moreover, it is possible to optimize the thickness of the surface graded layer and residual glass layer thereby providing the best combination of resistance to contact damage and flexural fracture for G/C/G FGMs.

Glass-ceramic powders are taught in U.S. Provisional Patent Application Ser. Nos. 60/860,165 and 60/858,234, the disclosures of which are herein incorporated by reference in their entirety. The present invention provides, in preferred embodiments, G/A/G structures having a thickness useful for dental applications. In many embodiments, the glass-ceramic powders used for infiltrating G/A/G contain one or more of, but are not restricted to, the following main oxides (i.e. at 1.0 weight percent or more): $SiO_2$, $Al_2O_3$, $TiO_2$, $Na_2O$, $K_2O$, ZnO, and $Rb_2O$. The composition of the infiltrating glass-ceramic can vary, as long as its CTE is similar to or preferably approximately the same as that of the alumina in a temperature range between the glass-ceramic transition temperature ($T_g$) and room temperature and the final product has an aesthetic appearance.

It is preferred to infiltrate a fully sintered alumina. The thickness of the graded glass-ceramic layer may be controlled by varying the infiltration temperature and duration.

The G/C/G system of the present invention suppresses both occlusal surface contact damage and cementation internal surface flexural damage. The G/C/G system of the present invention substantially overcomes the warpage or bending problems associated with the G/C systems of the prior art. The unique structure of the present invention G/C/G, which provides an outer surface residual glass layer, a graded glass-ceramic layer, and a dense interior ceramic provides the advantage that the aesthetic, veneering and cementation properties may be optimized. FGMs with low modulus glass ceramics at both top and bottom surfaces, sandwiching a high modulus, strong ceramic interior, improve the resistance to both contact and flexural damage. Such graded structures together with the outer surface residual glass layers may be utilized to enhance the aesthetic, veneering and cementation properties of polycrystalline dental ceramic cores.

The present invention is based in part upon the unexpected discovery that FGMs having surprisingly superior properties are produced when the sandwiched layer comprises alumina. It has been shown that continuously graded G/C composites, without significant internal stresses, may be produced by infiltrating glass into a dense ceramic surface where the two constituents G and C possess similar coefficients of thermal expansion (CTEs) and Poisson's ratio.

The present invention provides a G/C/G, in preferred embodiments, a G/A/G FGM produced by infiltrating the surfaces of dense alumina. By the term "dense" is meant that the powdered composition of the substrate has been subjected to an elevated temperature/time heating schedule, which would effect full densification of the compound. The new G/C/G, such as G/A/G composites offer better resistance to flexure-induced damage, better aesthetic, veneering and cementation properties over the existing commercial alumina cores.

Uniform graded layers on both top and bottom surfaces of dense alumina plates may be produced using glass infiltration techniques. These techniques may be readily used to fabricate graded structures on surfaces of orthopedic and dental prostheses with complex geometry.

Zhang et al. infiltrated partially sintered zirconia with aesthetic glass-ceramics, aiming to develop aesthetic, damage resistant, easy-to-cement all-ceramic dental crowns and bridges as described in U.S. Provisional Patent Application 60/858,234 filed Nov. 9, 2006, and a United States utility patent application filed on Nov. 9, 2007 claiming priority to the same, the disclosures of which are herein incorporated by reference in its entirety. The glass—porous ceramic infiltration approach is significantly different from the current concept—glass infiltration of fully dense ceramics. In preferred embodiments of the present invention, alumina is used because it is still the most commonly used ceramic material in orthopedics to date, and it represents a class of engineering ceramics, such as $Si_3N_4$, sialons, MgO, spinel, and alumina-zirconia composites, that can be infiltrated in a fully dense state.

The data indicate that a G/A/G structure exhibits better contact, sliding, and flexural resistance compared to monolith alumina (FIG. 5) under single-cycle loading conditions. (Jitcharoen et al., *J. Am. Ceram. Soc.* 1998;81(9):2301-8; Suresh et al., *Acta Materialia* 1999;47(14):3915-3926).

An elastically graded material, comprising a mixture of glass and a strong, dense, fine-grain, polycrystalline alumina, can be fabricated by glass infiltration. Since glass and alumina can be chosen with essentially the same CTE and Poisson's ratio, an increase in elastic modulus from surface glass-ceramic to a strong alumina interior can be engineered without introducing significant residual stresses. The G/A/G FGM structure produced in this manner can offer a much better resistance to contact, sliding, and flexural damage than either constituent alumina or glass as FIG. 5 demonstrates. In addition, by controlling the glass infiltration temperature and duration, it is possible to tailor the penetration depth of glass into the alumina surface, permitting the evaluation of the dependence of damage resistance on the thickness of the surface graded layer while maintaining the total thickness of the G/A/G structure constant. The glass infiltration method to produce FGMs is potentially applicable to a broad range of ceramic materials, including $Si_3N_4$, sialons, MgO, spinel, and alumina-zirconia composites.

Fracture Mechanics Analysis

Damage in brittle ceramics loaded with a cylindrical or curved indenter was explored in detail in the late 1800s by Hertz who described characteristic fracture patterns called Hertzian or classical cone cracks (Hertz (1882) *J Reine und Angewandte Mathematik* 92:156-171; Hertz (1896) Hertz's Miscellaneous Papers. London, Chs. 5,6: Macmillan). Intense research concerning damage modes in brittle coatings on compliant substrates loaded on the top surface, emulating ceramic crowns on dentin, began in the late 1980s. Most of the tests were done under single-cycle loading with a hard sphere indenter. Several damage modes, summarized in FIG. 2 were identified and analyzed. They can be divided into two categories: top-surface (occlusal-surface) damages from near-contact stresses, and bottom-surface (cementation internal surface) damage from far-field flexural stresses.

Near-contact occlusal-surface fracture modes in brittle materials, including outer cone cracks and median cracks, formed by precursor quasiplastic deformation. Outer cone cracks (O, FIG. 2) initiate just outside the indenter contact area where the maximum tensile stress of Hertzian stress field occurs. Quasiplastic deformation forms beneath the indenter, producing grain boundary microcracks which coalesce and evolve into occlusal-surface median cracks (M, FIG. 2). For brittle dental ceramics like porcelain and alumina, classical cone cracks dominate.

Far-field cementation internal surface radial fractures (R, FIG. 2) result from tensile stresses generated during loading. Radial cracks are oriented normal to the plate surface and are susceptible to any flexural tensile stresses generated during function. Therefore, once initiated, they propagate sideward and upward, ultimately leading to fracture (Kelly (1999) *The Journal of Prosthetic Dentistry* 81(6): 652-61). In dental crowns, radial cracks are clinically evidenced as bulk fracture which is believed to constitute the primary mode of failure of all-ceramic crowns. The load to initiate these internal surface radial cracks ($P_r$) depends strongly on thickness and elastic modulus of the ceramic and substrate and is given by $P_r = B\sigma_c d^2/(\log E_c/E_s)$, where B is a constant, $\sigma_c$ is the flexural strength of the material, d is the ceramic layer thickness, $E_c$ is the elastic modulus of the ceramic, and $E_s$ is the elastic modulus of the supporting substrate.

Extensive testing of porcelains, aluminas, zirconias, and glass ceramics on compliant structures have provided the data that has ultimately lead to fundamental relationships concerning loads to damage initiation for outer, median, and radial cracks for this broad array of ceramic layers on compliant structure for clinically relevant thickness under single-cycle loading. While there is competition for all outer, median, and radial modes to develop, in general radial cracks are likely to initiate first in thin sections (<0.8-1.0 mm), outer and median to develop first in thicker sections. The next goal is to develop a material with improved resistance to all these damage modes and wear while not increasing the hardness, elastic modulus, and fracture toughness of the surface of the prostheses, to avoid excessive wear of the opposing tooth or crown.

Damage Resistance of FGMs

The theoretical framework concerning frictionless normal indentation of elastically graded materials from a point load or from different indenter geometries has been developed by Giannakopoulos and Suresh. Explicit analytical expressions have been developed to relate the indentation load P to the penetration depth h, the contact radius a, and contact pressure $p_0$, for a Young's modulus E which varies with depth z beneath the indented surface. Theory predicts that when the elastic modulus increases with depth, the stress fields for the power-law case are focused more in the interior than for the corresponding exponential case. Experimental studies showed when glasses infiltrate into a dense ceramic surface, the Young's modulus variation from surface to interior is best described by the power-law relation $E=E_0 z^k$, where $E_0$ is the reference Young's modulus at the surface and k is a dimensionless constant (Jitcharoen et al. (1998) *Journal of the American Ceramic Society* 81(9): 2301-8). Such elastic variation effectively transfers the maximum contact stresses into interior upon occlusion, resulting in much improved resistance to quasiplastic deformation and brittle fracture at or in the vicinity of the occlusal surface.

Figure 2A:
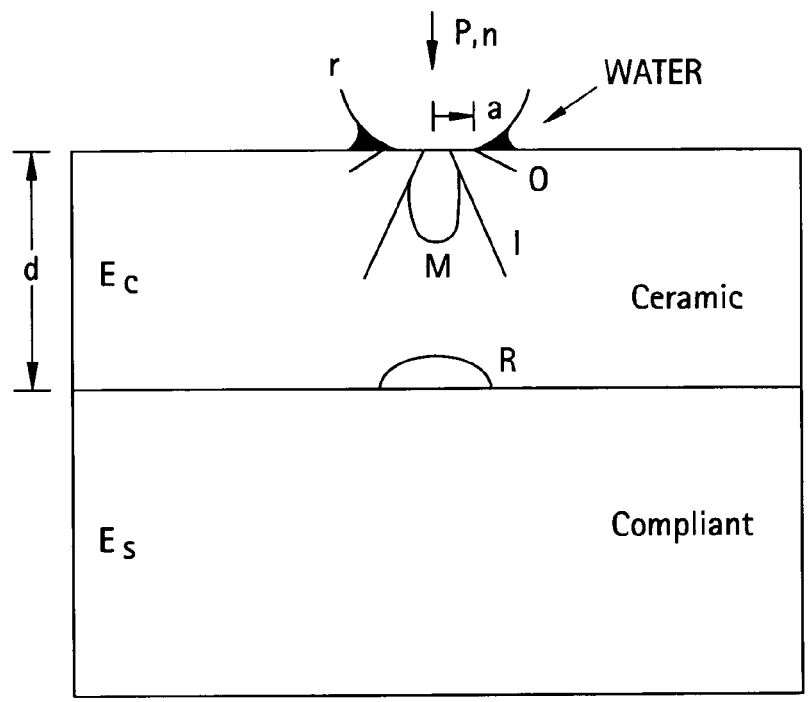
FIG. 2 is a schematic illustration of crack geometry for cyclic loading of (a) monolith ceramic coatings and (b) veneered ceramic layers on compliant substrates with sphere of radius r at load P in water. Near-contact surface damage modes: outer cone (O); inner cone (I); median crack (M). Far-field internal surface radial crack (R).
Figure 2B:
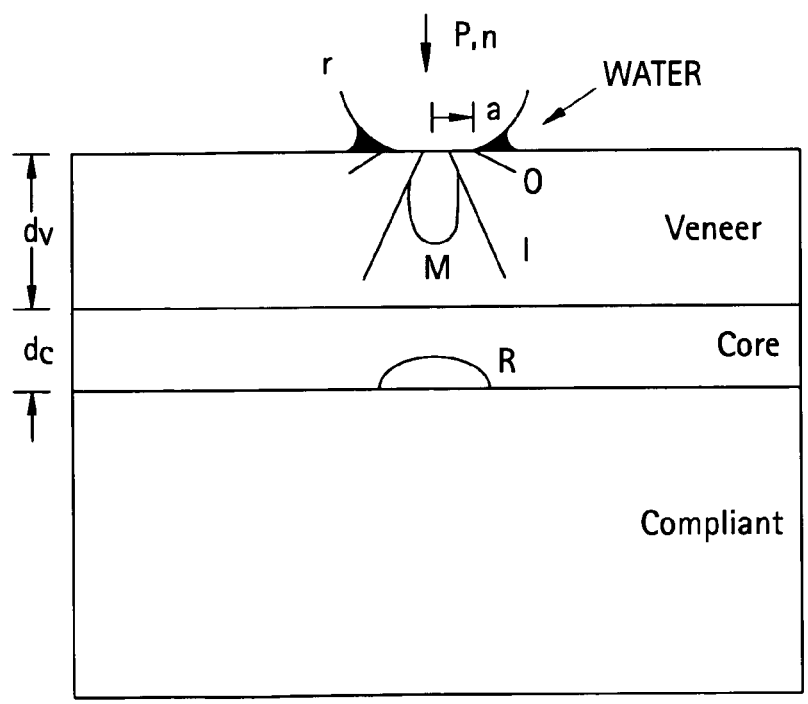

When a ceramic plate mounted onto a less stiff substrate (tooth-dentin) is subjected to loading from the top surface with a sphere indenter, the bottom surface of the ceramic plate experiences a maximum tensile stress which can result in bottom surface R cracking (FIG. 2). Finite Element Analysis (FEA) of FGMs with an increasing elastic modulus from the bottom surface to interior shows that the maximum tensile stress could be lowered by 20% compared to its bulk ceramic counterpart, even if the graded layer at the ceramic bottom surface is only 200 μm thick (Huang et al. (2007) *J Mater Sci Mater Med* 18(1):57-64). This is because the FGM at the bottom surface spreads the maximum tensile stresses from the surface into the interior. Therefore, if both top and bottom ceramic surfaces are graded, the damage modes shown in FIG. 2 can all be suppressed.

Ceramic crowns are vulnerable to near-contact and far-field flexure induced fracture from concentrated loading. Their vulnerability is exacerbated by damage, fatigue loading, and moisture. Although there has been immense amount of study concerning the fracture of ceramic crowns, the bulk of the work reported in the literature has focused on simple flexural strength tests under monotonic loading (Guazzato et al. (2004) *Dental Materials* 20: 449-456; Guazzato et al. (2004) *Biomaterials* 25: 5045-5052) or residual strength measurement following cyclic fatigue using load-to-fracture crushing test (Jung et al. (2000) *Journal of Dental Research* 79(2): 722-31; Stappert et al. (2005) *Journal of prosthetic Dentistry* 94(2): 132-139). These tests may not accurately predict the lifetime of real ceramic crowns, because most dental ceramics are susceptible to moisture assisted slow crack growth, which can result in a reduction in strength by 50% or more over a year or so (Zhang et al. (2004) *Journal of Biomedical Materials Research* 69B: 166-72). Also, ceramics are susceptible to cumulative mechanical damage during contact loading. It is important to systematically analyze fracture modes and damage evolution in ceramic layers in clinically-relevant testing—namely cyclic loading beneath a spherical indenter in a wet environment. A new damage mode, inner cone fracture, has been identified (FIG. 2). It is now well-appreciated that crack initiation and evolution is complex. Competing failure modes may develop on different surfaces, at different stages, and may interact depending on ceramic properties, layer thicknesses, and loading conditions (Zhang et al. (2005)*Journal of Materials Research* 20(8): 2021-9).

EXAMPLE 1

Manufacture

Using a glass tape infiltration technique, G/A/G structures may be fabricated. Alumina discs (CoorsTek, Golden, Colo.) were polished with successive grits to 1 μm finish on both circular faces to 25 mm in diameter and 1.5 mm in thickness for glass infiltration. A commercial glass tape (G-1002, Vitta Corp. Bethel, Conn.) was evenly applied to both circular faces of each alumina disc. Glass infiltration was performed inside a high temperature box air furnace (ST-1700C-6612, Sentro Tech Corp, Berea, Ohio). Various infiltration temperatures, ranging from 1400 to 1600° C., were used to fabricate a G/A/G FGM with different glass penetration depths. A constant dwell time of 1 hour and a heating and cooling rate of 600° C./hour were used. Thermal etching of alumina for 30 to 60 minutes at 50° C. below its sintering temperature of 1650° C. does not result in significant grain growth. This guideline was used to determine the upper limit of glass infiltration temperature.

Figure 3:
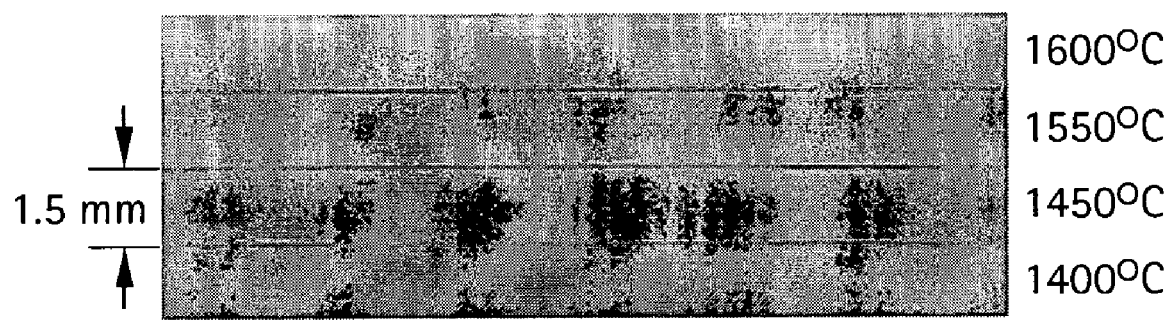
FIG. 3 is a digital photograph showing four G/A/G plates (d approximately 1.5 mm) infiltrated with glass tape at various temperatures for 1 hour in air.

G/A/G specimens following glass infiltration at various temperatures were cut through the center of the circular faces and stacked and epoxy mounted. The cross-sections were ground and polished for microscopy examination. FIG. 3 shows four of these G/A/G plates infiltrated with glass tape at various temperatures for 1 hour in air. The thickness of interpenetrated layers at both top and bottom surfaces varies with the infiltration temperature, being approximately 300 μm for 1400° C., 400 μm for 1450° C., 450 μm for 1550° C., and 550 μm for 1600° C.

Figure 4A:
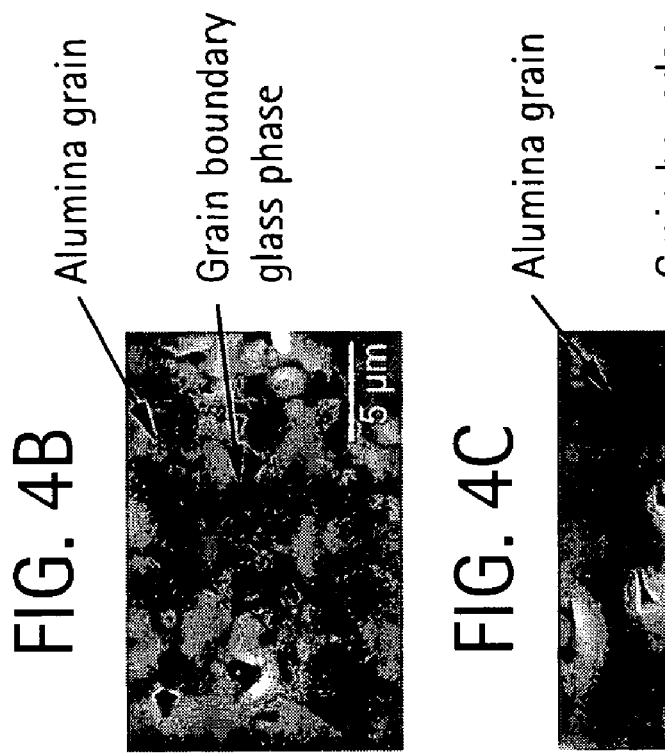
FIG. 4 shows scanning electron micrographs of a G/A/G composite following glass infiltration at 1600° C. for 30 minutes. The specimen was polished and etched with hydrofluoric acid solution (HF, 9.5%). (a) Low magnification view showing a G/A/G sandwich structure, d approximately 1.2 mm; (b) Surface graded glass-ceramic layer containing 45 volume % glass; and (c) Dense alumina interior. There is no significant residual glass layer on the surfaces of the G/A/G.
Figure 4A:
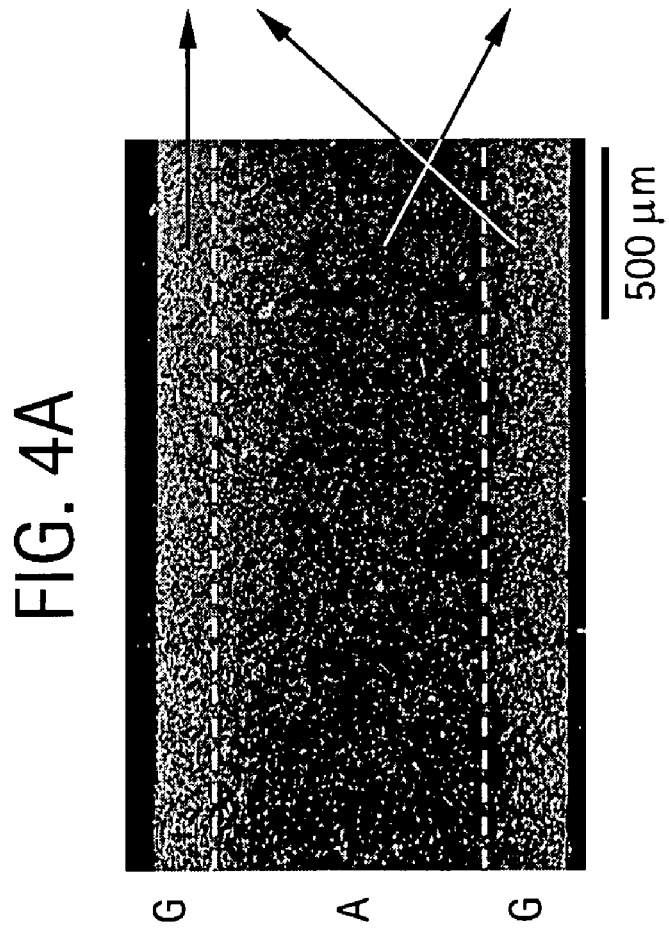

Scanning electron microscopy (SEM) of a cross-section G/A/G specimen (infiltration at 1600° C. for 30 min) revealed that the graded surface glass-ceramic layer consists of approximately 45 vol. % glass content while the interior comprises dense, high purity alumina (FIG. 4). The specimen was polished, etched with HF acid and carbon coated prior to SEM examination. In addition, a very small amount of residual glass was present on the surface of G/A/G FGMs fabricated between 1400° C. and 1600° C., indicating that the permeability of glass in dense, high purity alumina is very good at conditions tested here.

Figure 5:
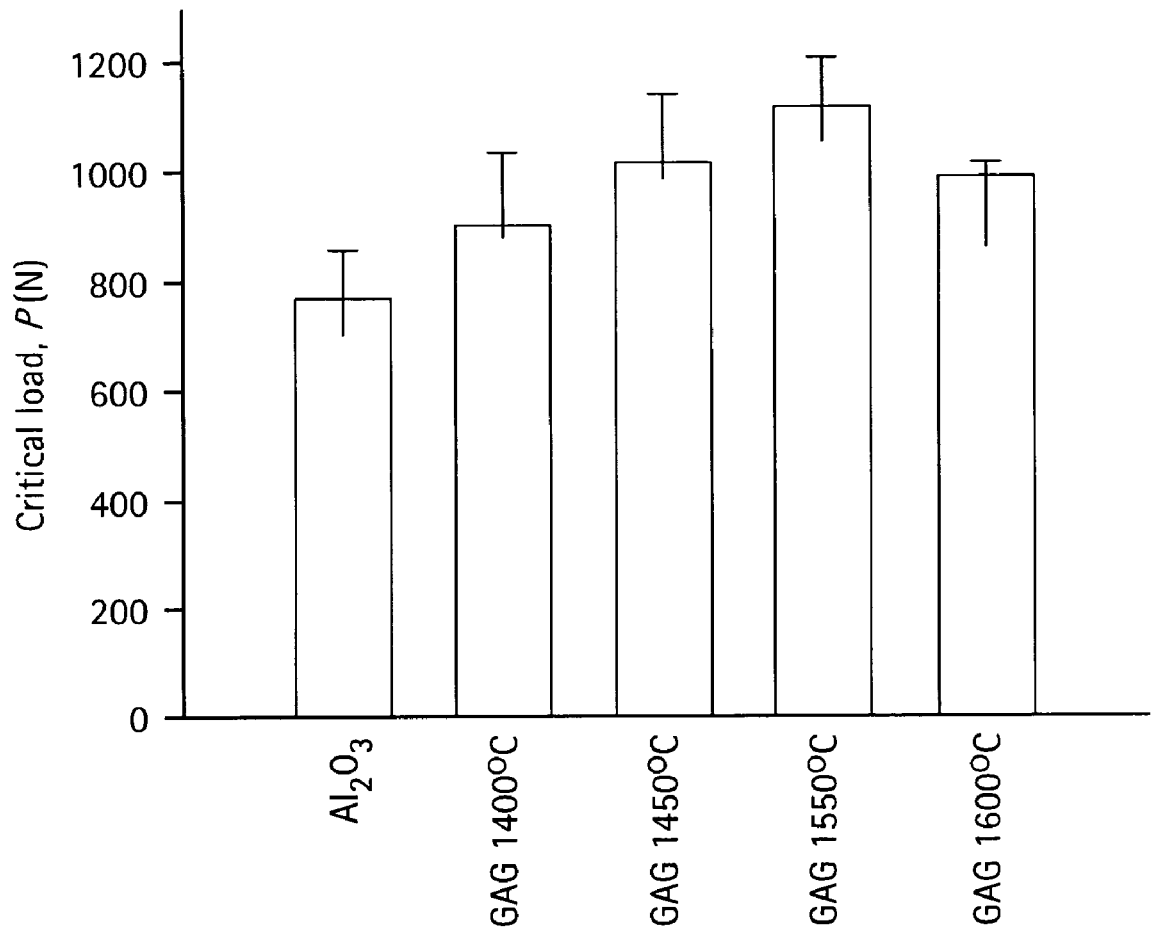
FIG. 5 is a bar chart showing critical loads for bottom surface radial cracking of ceramic plates (d=1.5 mm) on polycarbonate substrates. Ceramic plates include G/A/G fabricated at 1400, 1450, 1550 and 1600° C., as well as a homogeneous $Al_2O_3$.
Figure 6A:
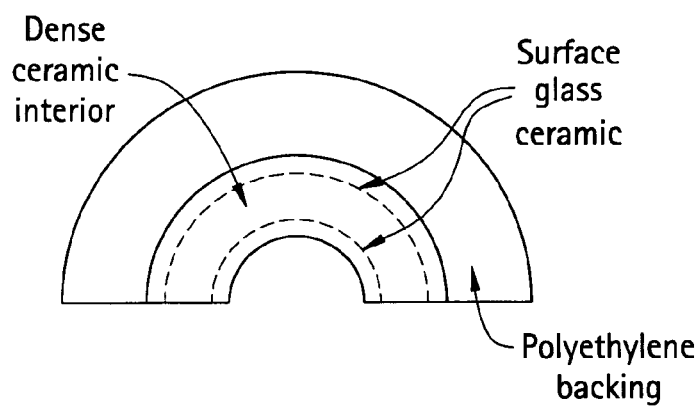
FIG. 6 is a schematic diagram illustrating a ceramic liner and a ceramic femoral head with (a) and (b) both surfaces graded or (c) and (d) only one surface graded for an orthopedic prosthesis. (e) Ceramic dental prosthesis (for both monolithic or core structures) with graded structures at surfaces subject to wear, contact, and impact.
Figure 6B:
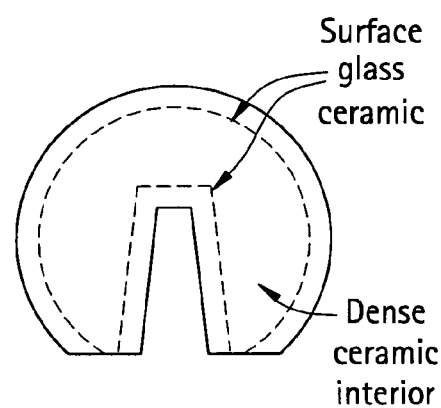
Figure 6C:
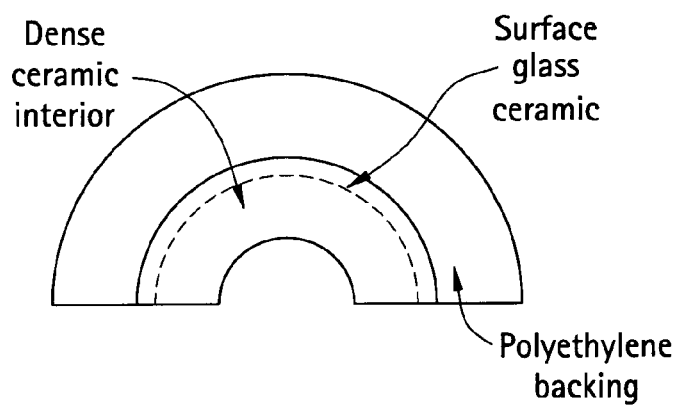
Figure 6D:
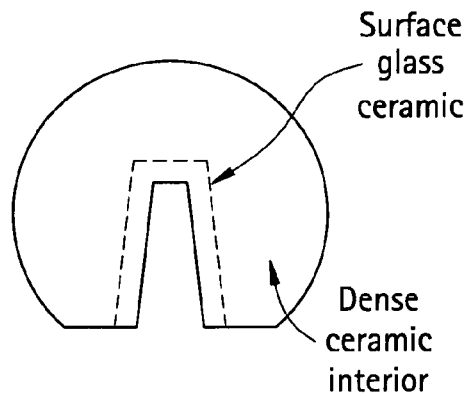
Figure 6E:
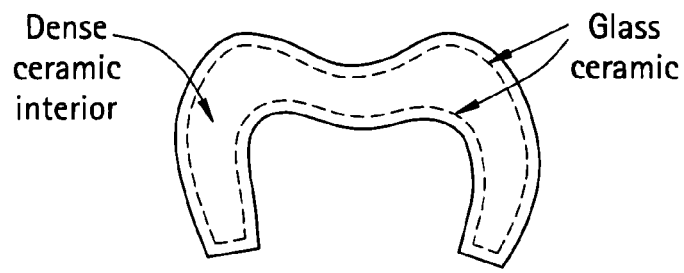

Critical loads to produce flexure-induced fracture at the bottom surface of G/A/G plates infiltrated at various temperatures, and their homogeneous alumina counterparts, were measured using a screw-driven Instron machine (Model 5566, Instron Corp., Canton, Mass.). G/A/G specimens and bulk alumina discs of 1.5 mm thick were polished to 1 μm finish and epoxy bonded to polycarbonate substrates. Each load was delivered through a WC sphere (r=3.18 mm) with a loading rate of 1 mm/min. Critical loads to produce radial R cracks were measured for bulk alumina and for G/A/G specimens fabricated from four different glass infiltration temperatures (FIG. 5). Each of the four glass infiltration conditions had a total of six specimens (n=6) fabricated in batches of three. Variations in critical loads between specimens fabricated from different batches were approximately 10%, similar to those prepared from the same batch. Critical loads, presented as means and standard error of the mean (mean ±SEM), for G/A/G infiltrated at 1550° C. are approximately 30% higher than those for bulk alumina, indicating that the G/A/G composites are approximately 30% more resistant to flexure-induced R fracture than the homogeneous alumina (FIG. 5). One-sample t-test demonstrates that it is highly unlikely (p<0.001) that a specimen as strong as G/A/G could have been sampled from the population of homogeneous alumina.

EXAMPLE 2

Materials and methods. A damage resistant G/A/G structure is fabricated using a glass-ceramic infiltration technique. Glass tape approximately 1 mm thick (CTE=7.0×10$^{-6}$ m/m ° C., Vitta G-1002) is applied to both circular faces of a finely polished medical/dental grade alumina plate (φ12 mm×1.6 mm or φ12 mm×0.8 mm, CTE=7.0×10$^{-6}$ m/m° C.) (Nobel Biocare, Göteborg, Sweden). Infiltration occurs inside a high temperature box air furnace (ST-1700C-6612, Sentro Tech Corp) to create a G/A/G structure (FIG. 3). A heating and cooling rate of 500° C./hour is employed. By varying the glass infiltration temperature from 1000-1600° C., it is possible to control the glass penetration depth. The excess glass-ceramic may be ground away from both surfaces of the G/A/G structure, and the surfaces may be polished to 1 μm finish.

The microstructural gradation of the G/A/G structure may be examined using combined optical and SEM on the cross-section of the specimens. The plates may be sectioned using a thin diamond saw (0.3 mm thick, Leco Corp., St. Joseph, Mich.). The cross sections may be ground and polished to 1 μm finish and etched with 9.5% HF acid at room temperature, then carbon coated for SEM examination and energy dispersive X-ray (EDX) analysis.

The dependence of elastic modulus gradation on the depth (from both top and bottom surfaces to interior) may be determined using a depth control Nanoindenter (Nanoindenter XP, MTS Systems Corp., Oakridge, Tenn.) at NIST. Indentation may be made on polished cross sections of the G/A/G structure. A penetration depth of 2 μm may be used to produce an indentation impression with a lateral dimension of approximately 15 μm. Since the average grain size of the biomedical alumina is 5 μm or less, a lateral indentation impression of 15 μm probes several grains in a dense alumina region and 2-3 adjacent grains at the surfaces. Elastic modulus may be determined 20 μm at each step from the surfaces to the interior, with six indents for a particular depth.

Residual stresses in the graded G/A/G structure may be evaluated using the methods taught by Jitcharoen et al., *J. Am. Ceram. Soc.* 1998;81(9):2301-8. The methods include infiltrating one surface of a 4 mm thick alumina plate with aluminosilicate glass at 1690° C. in air for 2 hours to produce a thick graded surface of 2 mm, comparing the difference in the lengths of Vickers radial cracks in the surface of the glass/alumina FGM and in a control bulk alumina ceramic that contains the same amount of glass as the FGM surface. There is no significant difference in the lengths of radial cracks in the two cases, indicating that no significant residual stresses are present on the FGM surface. The depth of the Vickers indentation is much smaller than the scale over which the gradation of the elastic modulus occur. Thus the indentation saw the FGM as a bulk alumina containing the same amount of glass as the FGM surface. (Jitcharoen et al., *J. Am. Ceram. Soc.* 1998;81(9):2301-8)

Results. An elastically graded G/A/G structure without significant residual stresses is synthesized using the glass infiltration technique. The microstructure of the G/A/G structure varies from surface to interior as the glass content decreases. As a result, the elastic modulus increases from surface to interior. The G/A/G structure provides an ideal system for establishing the structure-property (structure-contact, sliding, and flexural resistance) relation of FGMs.

EXAMPLE 3

G/A/G structures of various thicknesses of graded layers at both top and bottom surfaces may be used to systematically investigate the damage response of FGMs to single- and multi-cyclic loadings using spherical indenters with and without a sliding component, aiming to establish the structure-property relation of FGMs. This is based upon previous studies in which an alumina plate (4 mm thick) with one of its surfaces graded with aluminosilicate glass (2 mm thick) exhibited improved resistance to contact damage from normal single cycle loading at 3000 N, as well as from single path sliding at 800 N, relative to both bulk alumina and aluminosilicate glass. There is an optimized thickness of the surface graded layers that results in a best combination of resistance to contact, sliding, and flexural damage.

Materials and methods. A G/A/G structure with two final dimensions may be fabricated: φ12 mm×1.6 mm or φ12 mm×0.8 mm. Three groups of specimens with different graded glass-alumina layer thicknesses may be fabricated for G/A/G of 0.8 mm in total thickness, and six groups with different graded layer thicknesses for G/A/G of 1.6 mm thick (Table 1). Maintaining an equal thickness of the graded layer at the top and bottom surfaces for each specimen prevents warpage. The effect of graded layer thickness on damage resistance for G/A/G structures having different thicknesses may be elaborated by comparing specimen groups Tn1, Tn2, Tn3 with Tk1, Tk2, Tk3. The effect of relative ratio of the graded layer and the total specimen thickness on the damage resistance may be examined by comparing specimen groups Tn1, Tn2, Tn3 with Tk2, Tk4, Tk6. Tn and Tk represent "thin" and "thick" specimens, respectively.

TABLE 1

Design parameters for a G/A/G with various thicknesses of graded layers.

| | Total G/A/G thickness (mm) | | | | | | | | |
|---|---|---|---|---|---|---|---|---|---|
| | 0.8 | | | 1.6 | | | | | |
| Graded layer thickness (mm) | Tn1 | Tn2 | Tn3 | Tk1 | Tk2 | Tk3 | Tk4 | Tk5 | Tk6 |
| Top surface | 0.1 | 0.2 | 0.3 | 0.1 | 0.2 | 0.3 | 0.4 | 0.5 | 0.6 |
| Bottom surface | 0.1 | 0.2 | 0.3 | 0.1 | 0.2 | 0.3 | 0.4 | 0.5 | 0.6 |

G/A/G structures having both surfaces polished may be epoxy bonded to a polycarbonate substrate and subjected to single-cycle-load strength measurement in a wet environment using an Instron universal testing machine (Model 5566, Instron Corporation, Canton, Mass.). In a single-cycle-load test, a monotonically increasing load delivered through a 3.18 mm radius WC sphere may be applied on the top surface of the G/A/G structures. The loading rate may be 1 mm/min. Loads may be applied until fracture of the G/A/G layer occurs. Fracture may be captured using a video imaging system. Loads to fracture may be recorded and analyzed.

The strongest group from the single-cycle-load strength screen results for both thick and thin samples may be chosen for cyclic fatigue test in water. Monolith alumina plates having the same thicknesses as the G/A/G structures may be used as controls. Polycarbonate may be used as a substrate material because it is transparent, thus permitting direct observation of fractures propagating to or from the bottom surface of the G/A/G layer. Fatigue loading may be delivered with a 3.18 mm radius WC sphere at 1 Hz using a mouth-motion simulator (Elf 3300, Bose Corporation). To facilitate direct comparison of damage under normal contact (uniaxial) and contact-slide (biaxial) fatigue loading, two loading profiles may be utilized. In uniaxial fatigue, each load cycle consists of the indenter contacting the specimen, loading to a maximum, holding for 0.5 seconds, unloading, and lifting off (0.5 mm) from the structure surface. The entire stroke profile may be restricted to a vertical axis. In biaxial fatigue, each load cycle consists of the indenter contacting the specimen, loading to a maximum, holding the maximum load for 0.5 seconds while the specimen moves laterally at a constant velocity v=2 mm/s for 1 mm, and then returning the specimen to its original position during lift off. Failure of the G/A/G layer is defined as any near-contact top surface damage that penetrates through the entire layer and reaches the G/A/G and polycarbonate interface or the bottom surface radial fracture is observed. Both fracture modes can be observed directly by the imaging system.

To construct failure maps for G/A/G on compliant substrates, fatigue tests may be conducted using maximum load levels at 90%, 80%, 70%, 60%, and 50% of the single-cycle fracture load. Five repeats are proposed for each prescribed load level, to check reproducibility. Three repeats per load level are usually adequate for demonstrating the competition between the various damage modes, and for gaining significant predictability of lifetimes for each mode. (Bhowmick et al., *Journal of Materials Research* 2005;20(10):2792-2800; Zhang et al., *Journal of Materials Research* 2005;20(8):2021-9; Hermann et al., *Journal of Materials Research* 2006;21(2):512-521) Samples subject to 1 million cycles fatigue loading without failure may be considered as "survivors". Previous fatigue studies on (ungraded) Coors medical grade alumina and Norton Y-TZP on polycarbonate substrates show that all specimens survived 1 million loading cycles when the applied maximum load levels fell below 50% of the single-cycle fracture load. (Zhang et al., *Journal of Biomedical materials research* 2005;72B:388-92; Zhang et al., *Journal of Biomedical Materials Research* 2004;71B(1): 166-71; Zhang et al., *Journal of Biomedical materials research* 2004;71B(2):381-6)

Surviving specimens may be randomly selected and sectioned to evaluate the extent of subsurface damage. Failure maps may be constructed from the experimental fatigue data. These maps graphically summarize the relative timing of different failure modes as a function of load and number of fatigue cycles. They provide easy visualization of the important load-fatigue life-damage modes relation. This summary information is valuable in planning fracture resistant strategies for design applications. The fracture surface of randomly selected G/A/G specimens may be analyzed to determine the effect of a glassy phase on crack path in the graded alumina at grain level. A SEM (Hitachi 3500N) equipped with an energy-dispersive spectroscopy (PGT IMIX) and a backscatter electron imaging detector may be utilized to reveal the crack-microstructure interaction. For comparison, crack paths in homogeneous alumina ceramics may also be examined. In addition, controlled cracks and damage may be produced in glass-alumina graded layers and the dense alumina layer using Vickers and Hertizan indentations. Crack tip-microstructure interaction and quasiplastic deformation of graded structures may be investigated compared to homogeneous alumina.

For cyclic fatigue tests, Weibull statistics may be used for data analysis. No overlap of the 90% two-sided confidence bounds may be considered as significant. For single-cycle-load strength tests, data may be input to SPSS (ver. 12.0), a statistical analysis program, and after checking for accuracy, may be summarized as means and standard deviations by group. Assuming that within-group variances are homogeneous between groups, data may then be analyzed in a 1-way ANOVA. If a significant omnibus test results (i.e. $p<0.05$), post-hoc t-tests may be used to identify particular samples that differ from one another.

Results. In a homogeneous ceramic plate on polycarbonate bilayer, fatigue cycling reduces the strength of the specimen. (Zhang et al., *Journal of Biomedical Materials Research* 2004;71B(1):166-71) In as-polished alumina and Y-TZP bilayer specimens, continual growth of bottom surface radial R cracks reduce strengths by 50% within the equivalent of 1 year of cyclic loading (n approximately 30,000,000). Similar degradation trends will be found in the G/A/G structure on polycarbonate specimens, but with longer life expectation in G/A/G, i.e. at the same load level, a larger number of cycles will be required to initiate and propagate R cracks. Also, hydraulically-driven I cracks, quasiplasticity-associated M cracks, and friction-activated partial cone cracks will develop in a G/A/G under uniaxial and biaxial fatigue, in wet environments, but at higher loads or larger number of cycles than in their homogeneous constituents. The propagation/penetration rate of I, M, and partial cone cracks will be much slower in G/A/G than those in homogeneous ceramics. Failure maps for G/A/G structures on polycarbonate bilayers for fatigue loading with or without a sliding action will be developed. A thickness of surface graded layer that results in a balanced contact and flexural damage will be determined.

While the present invention has been set forth in terms of specific embodiments thereof, it will be understood that numerous variations upon the invention are now enabled to those skilled in the art, which variations yet reside within the scope of the present teachings. Accordingly the invention is to be broadly construed and limited only by the scope and spirit of the present disclosure.

The invention claimed is:

1. A functionally graded glass/ceramic/glass composite structure comprising an underlying graded glass-ceramic layer, and a dense interior ceramic wherein a top and a bottom surface of the ceramic are infiltrated with glass.

2. A functionally graded glass/ceramic/glass composite structure according to claim 1 further comprising an outer residual glass layer.

3. A functionally graded glass/ceramic/glass composite structure in accordance with claim 1, substantially non-susceptible to warping or bending.

4. A functionally graded glass/ceramic/glass composite structure in accordance with claim 1, wherein the underlying ceramic comprises alumina.

5. A functionally graded glass/ceramic/glass in accordance with claim 4 wherein the coefficient of thermal expansion (CTE) of the glass is substantially the same as the coefficient of thermal expansion of the alumina.

6. A functionally graded glass/ceramic/glass in accordance with claim 1 further comprising a veneer on an outer surface.

7. A medical or dental prosthesis comprising a functionally graded glass-ceramic/ceramic/glass-ceramic composite structure wherein a top and a bottom surface of the ceramic are infiltrated with glass.

8. A medical or dental prosthesis comprising a functionally graded glass-ceramic/ceramic composite structure wherein a top and a bottom surface of the ceramic are infiltrated with glass.

9. A medical or dental prosthesis according to claim 7 wherein the ceramic comprises alumina.

10. A medical or dental prosthesis according to claim 7 selected from the group consisting of an aesthetic and damage-resistant ceramic orthopedic prosthesis, an orthopedic stem, an orthopedic or dental anchor, an orthopedic or dental implant, a dental prosthesis, and an endodontic post.

* * * * *